United States Patent [19]

Ishida et al.

[11] Patent Number: 4,522,721
[45] Date of Patent: Jun. 11, 1985

[54] TREATING PROCESS OF ORGANIC WASTES

[75] Inventors: Masahiko Ishida; Ryoichi Haga, both of Hitachi, Japan

[73] Assignee: The Agency of Industrial Science and Technology, Tokyo, Japan

[21] Appl. No.: 579,009

[22] Filed: Feb. 10, 1984

[30] Foreign Application Priority Data

Feb. 15, 1983 [JP] Japan .................................. 58-22119

[51] Int. Cl.$^3$ .............................................. C02F 3/28
[52] U.S. Cl. ..................................... 210/603; 210/610
[58] Field of Search ............... 210/603, 610, 612, 613, 210/615–618, 630, 631, 919

[56] References Cited

U.S. PATENT DOCUMENTS

| 4,323,367 | 4/1982 | Ghosh | 210/603 X |
| 4,329,428 | 5/1982 | Ghosh et al. | 210/603 X |
| 4,386,159 | 5/1983 | Kanai | 210/603 X |

*Primary Examiner*—Thomas Wyse
*Attorney, Agent, or Firm*—Birch, Stewart, Kolasch & Birch

[57] ABSTRACT

The present invention relates to a treatment process of anaerobically digesting organic wastes under an anaerobic condition for recovering methane from the organic wastes by fermentation effect of anaerobic bacteria. This treatment process is carried out by the charging organic wastes of 50~70% water content and seed digestives alternately in strata in a digestion tank and then keeping the interior of said digestion tank under an anaerobic condition.

4 Claims, No Drawings

TREATING PROCESS OF ORGANIC WASTES

BACKGROUND OF THE INVENTION

The present invention relates to a process of treating organic wastes, and, in particular, it is concerned with a organic waste treating process which recovers methane from organic waste by the fermentation effect of anaerobic bacteria.

In the past, an anaerobic digestion process has been employed for treating organic wastes such as sewage sludge and food processing drainage, etc. This process has advantages not only in its suitability to treat wastes which have high water content or have difficulties in incineration, but also has a feature facilitating the recovery of methane as a source of clean energy, and recently active studies are being pursued for its application to city garbage and agricultural wastes. In most of such instances relating to the treatment of sewage sludge and human and livestock wastes which are in slurry form, they are being treated as they are, while in the case of city garbage and agricultural wastes they are being subjected to digestion after they are turned into slurry form by adding water thereto. In other words, in the practical sense, sewage sludge and human and livestock wastes are treated in their original slurry form, while city garbage and sewage sludge dehydrated cake are digested by so-called liquid culturing after being turned into liquid slurry by adding water thereto (e.g. in the method described in Japanese Published Unexamined Patent Application, Ser. No. 134002, Showa 53 Gazette, the subject of treatment is treated after it is turned into a slurry of 90~92% water content, or gruel type wastes).

According to this kind of process, however, the dimensions of the digestion tank to be employed are necessarily large due to the required dilution of the wastes by water. Therefore, much more energy is required for heating the water in the slurry up to fermentation temperature and much of electric power is required for stirring the slurry during the period of time the fermentation is being performed. Further, significant amounts of energy and expenses are required for dehydration of the digested slurry and disposal of final waste water. In addition, this approach has the additional disadvantage in that it tends to give rise to scum over the liquor surface and to sedimentation and solidification of sand and pebbles at the tank bottom.

If, therefore, these wastes could be digested in their solid state as they are, the dimension of the digestion tank could be made smaller, disposal of final waste water could be dispensed with and a wide reduction could be attained in the energy consumed. Thus, these problematic areas could be eliminated. As a result of various studies relating to solid state fermentation which does not require the turning of waste into slurry, applicants have confirmed the following points.

(1) In the case where the organic capacity load is extremely low, such as not more than $0.05$ kg.VS/$m^3$.d, fermentation is possible with or without stirring;

(2) However, if stirring is performed within the tank, the load could be increased to $0.2$ kg.VS/$m^3$.d; and (3) If the load is set at over $0.2$ kg.VS/$m^3$.d, the waste under treatment becomes acidic and the generation of methane drastically reduced, or at worst, it stops generation.

Accordingly, the solid state fermentation would be possible if such conditions are taken into consideration, but operation under a load of around $5$ kg.VA/$m^3$.d, comparable to that of conventional slurry fermentation, becomes very difficult.

In this case (load of $5$ kg.VS/$m^3$.d), stirring the solids within the tank not only requires very much energy, as compared with stirring wastes in slurry form, but also an exceedingly large burden is placed on the digestion tank and the stirring mechanism. Therefore, not to mention the case where the objective is to conserve energy, even in the case where the waste treatment is the only objective, its practicability is judged to be low.

Generally in an anaerobic digestion, it is known that the organic matters contained in the feed wastes only decompose into methane when passed through two different fermentations, i.e. first, a liquefying fermentation wherein the organic matters are turned into such volatile fatty acids of low molecular weight as acetic acid, propionic acid and butyric acid by the effect of facultative anaerobic bacteria (liquefying bacteria or septic bacteria), and second, gasifying fermentation wherein thus generated fatty acids are converted into methane through the effect of obligatory anaerobic bacteria (gasifying bacteria or methane bacteria). The digestion process presently being practised in general is a mixed fermentation method which carries out a parallel-dual fermentation within the fermentation tank under the co-presence of these two bacteria groups. In this case, the optimum pH range for the liquefying fermentation exists in the range of acidic to neutral, whereas that for the gasifying fermentation is somewhere from neutral to weak-alkaline range. For this reason, the liquefying fermentation is performed around the neutral range, but the fermentation speed of the gasifying fermentation is less than that of the liquefying fermentation. Therefore, if the operation is performed under an overloaded condition within the tank, there is the risk that the gasifying fermentation might be brought to a halt by a lowered pH within the system as the fatty acids accumulate.

SUMMARY OF THE INVENTION

Based on this theory, applicants have made a further study as to the possibilities of solid state fermentation with no stirring, and, as a result, have discovered that, even attempting to carry out fermentation under a relatively high load of $1$ kg.VS/$m^3$.d while stirring the contents of the tank, almost no methane is generated due to acidification within the system, but when the feedstock and seed-digestives are placed into the fermentation tank without mixing and are subjected to fermentation as the ununiform composition, the generation of methane continues.

Then, in a 3 l ($160$ $\phi \times 150$ mm) fermentation tank made from transparent acrylic resin, a 5 cm thick layer of seed digestives, next a 3 cm thick layer of feed wastes and a 5 cm thick uppermost layer of seed digestives were placed in strata from the bottom upward in that order and they were kept anaerobically at $60°$ C. Pulverized city garbage was used as the feed wastes, and digestion sludge dehydrated cake of pulverized city garbage in a liquid slurry form as seed digestives. As a result, with an uninterrupted generation of methane, the color of the feed wastes layer turned from grayish brown to yellowish brown which is characteristic of liquefying fermentation, and simultaneously the color of the boardering areas between the seed digestives and the feed wastes layers turned to black which is characteristic of methane generation. Also, upon checking the depthwise pH distribution, the feed wastes layer turned to acid after one day, and, at the same time, the boardering areas between the seed digestives and the feed wastes layers remained at around a pH of 6.8. Then, it was observed that the pH of the feed wastes layer returned to neutral after four days. From the above phenomena, it was assumed that the generation of methane was taking place at the boardering areas of the respective layers. In other words, it is believed that unimpeded gasifying fermentation at the seed digestives layers permits the generation of methane to continue, as the whole areas of the seed digestives layers do not turn acidic even though fatty aids are generated at the feed wastes layer.

The present invention was achieved on the basis of the aforementioned knowledge, and its objective is to offer a method whereby organic wastes are anaerobically digested efficiently, without turning them into slurry form, retaining the wastes in a solid state as they are, without stirring the contents of the digestion tank.

The gist of the present invention is, in the method of unaerobically digesting organic wastes under an unaerobic condition, a process for treating organic wastes which is characterized by placing alternately a layer of organic wastes containing 50~70% water and a layer of seed digestives in strata in the digestion tank and keeping the interior of the digestion tank under an anaerobic condition.

DETAILED DESCRIPTION OF THE PREFERRED EMBODIMENTS

The present invention will become more fully understood from the detailed description given below but such is not intended to limit the scope of the present invention.

The present invention is characterized by placing alternately solid feed organic wastes having a certain specified water content and seed digestives in strata and digesting them under an anaerobic condition without stirring them.

In this present invention, as the feed wastes, microbial decomposable ingredients, for example such solid organic wastes as containing starch, protein, fat, cellulose, etc., to be practical, city garbage, agricultural wastes, dehydrated organic sludge, etc. may be used. The water content of the feed wastes is to be within the range of 50~70%. In the case of using a feedstock having a water content greater than 70%, as the liquefying fermentation progresses, acidic liquor containing fatty acids precipitates through and down the layers and turns the seed digestives layer underneath acidic whereby gasifying fermentation will be impeded. In addition, it is not desirable as it makes the fermented gas difficult to remove from the system. Also, when the feedstock contains not more than 50% water fermentation will be hampered.

The process of the present invention is not limited to specific anaerobic bacteria, and a mixture of normal liquefaction bacteria and gasification bacteria may be used. As the liquefaction bacteria, for example, those which belong to Clostridium genus, Bacillus genus and Escherichia genus may be used. For the gasification bacteria which convert volatile fatty acids into methane, for example, those which belong to Metanococcus genus, Methanosarcina genus and Metanobacterium genus may be used.

In the present invention, the conditions for fermentation can sufficiently be met by those which are publicly known so far. Namely, as the fermentation temperature, normally 15°~70° C., and for the oxidation-reduction potential, not more than −200 mV are desirable.

The way of charging or discharging feedstock may be similar to conventional methods, and an advantage is that the digested feedstock after fermentation can be recycled for reuse as seed digestives.

The surplus of digestive matters can be effectively used in a similar manner as those from the conventional processes, but they are most stable and show equal or much more effect as organic fertilizer than the digestion sludge separated from the digestion slurry of the conventional processes. Moreover, whereas such organic ingredients as ammonia, potassium and phosphoric acid are lost in the form dissolved in the treated water in case of the conventional slurry digestion, in the solid state fermentation of the present invention, it does not accompany any loss of organic ingredients.

Of the fermented gas, the volume of methane generated differs depending on the nature of the feed organic wastes, fermentation conditions and species of fermentation bacterium employed, but 200~320 l per 1 kg of organic wastes can be made available. The composition of the fermented gas generally contains methane 40~80%, carbon deoxide 20~60% and, in addition, trace amounts of hydrogen, nitrogen and hydrogen sulfide are involved. The fermented gas thus obtained can also sufficiently be used as fuel for the heating boiler for heating the fermentation tank and for the gas electric generator for the stirrer.

Hereinafter, the present invention is described by way of the accompanying examples, but is not intended to be limited to the following preferred embodiments.

PREFERRED EMBODIMENTS 1~3

A cylindrical fermentation tank of 8 l effective dimension (80$\phi$×200 mm) with warm water jacket, was charged with pulverized city garbage (kitchen wastes 28%, paper scraps 58%, plastics wastes 5%, and glass wastes/pebbles 9%) and the seed digestives which were the product of having anaerobically digested the above city garbage at 60° C. alternately each other in strata. While fixing the charged volume of the seed digestives at 1 l, three sets of experiments were conducted with the charged volume of feed city garbage at 0.2, 1.0 and 5.0 l respectively. The layer thicknesses of the seed digestives and the city garbage are shown in the next table. The feed city garbage had a 0.40 bulk specific gravity, a 65% water content and a 70% organics content (dry basis). The seed digestives had a 0.56 bulk specific gravity and a 65% water content. After replacing the air in vapor phase by argon gas which was charged into the fermentation tank from its bottom, the interior of the tank was kept under an anaerobic condition at 60° C. At the same time of measuring the gas volume generated during fermentation, the volume of methane generated was measured by analyzing the methane concentration. In the table, as the records of the respective fermentation experiments, other than the methane yield (l—$CH_4$/kg VS) and the number of days required for fermentation (d), there indicated are the efficiency of methane generation in the fermentation tank ($m^3$—$CH_4$/$m^3$—fermentation tank/d—the required days) and the efficiency of treating feedstock in the fermentation tank (t-feedstock/$m^3$-fermentation tank-/d—the required days).

COMPARATIVE EXAMPLE 1

In a cylindrical fermentation tank of 20 l effective dimension equipped with stirring blades and a warm water jacket, 0.4 kg of slurry (solid concentration 7%) made of 0.2 l (0.08 kg) of the city garbage taken from the identical batch which was used in the Preferred Embodiments mixed with 0.32 kg of water was charged. Then, next, a slurry (2.8 kg) (solid concentration 7%) made of 1 l (0.56 kg) of the seed digestives taken from the identical batch which was used in the Preferred Embodiments mixed with 2.24 kg of water was added thereto, and, after replacing its vapor part with argon, fermentation was performed under an anaerobic condition at 60° C., with stirring at 200 rpm, whereby the records shown in the table were obtained.

COMPARATIVE EXAMPLES 2 AND 3

The following two sets of experiments were performed with the identical type fermentation tank as employed in the Preferred Embodiments and the city garbage as well as the seed digestives taken from the identical batches which were used in the Preferred Embodiments. Two composites, one was made of 0.1 l of city garbage as against 1 l of seed digestives and the other 0.2 l of city garbage as against 1 l of seed digestives, were charged respectively into the fermentation tank, and, after replacing the air within the tank with argon, they were kept respectively at 60° C. under an anaerobic condition. The respective fermentation performances are shown in the table.

COMPARATIVE EXAMPLES 4~7

By installing a spiral stirring blade of a 70 mm$\phi$ diameter 700 mm long and 1 pitch 70 mm in the fermentation tank of the size identical to that which was employed in the Preferred Embodiments, the following experiments were carried out. In four cases, where the city garbage of 0.2, 0.5, 1.0, and 5.0 kg respectively were added to 1 l of the seed digestives (common to all four), the temperature was kept at 60° C. under an anaerobic condition while stirring at 25 rpm. The respective records of fermentation are shown in the table.

The Preferred Embodiments of the present application excel in both the efficiency of methane generation in the fermentation tank and the efficiency of feedstock treatment, as compared with the conventional slurry fermentation (Comparative Example 1). Further, in case where the solid state fermentation is performed on the mixture of the feedstock and the seed digestives without stirring, fermentation can be performed when the load is very low (Comparative Example 2), whereas fermentation is impeded when the load is identical to that of the Preferred Embodiment 1 (Comparative Example 3). Therefore, both the efficiency of methane generation in the fermentation tank and the efficiency of feedstock treatment are falling short of the Preferred Embodiments. In the meantime, in case where the mixture of the feedstock and the seed digestives is subjected to fermentation with stirring, when the load is identical to that of Preferred Embodiment 1 (Comparative Example 4) fermentation can be performed, but when the load is raised thereabove (Comparative Example 5~7) fermentation is impeded. For these reasons, their fermentation efficiency in the fermentation tank as well as the efficiency of feedstock treatment are inferior to those of the present application.

TABLE

| | | Preferred Embodiments | | | Comparative Examples | | | | | | |
|---|---|---|---|---|---|---|---|---|---|---|---|
| | | 1 | 2 | 3 | 1 | 2 | 3 | 4 | 5 | 6 | 7 |
| Fermentation Method | | | | | | | | | | | |
| Fermentation Process Charged Volume | | Solid State Fermentation | | | Slurry Fermentation | Solid State Fermentation | | | | | |
| | Feedstock (l) | 0.2 | 1 | 5 | 0.2 (7% Slurry 0.4 kg) | 0.1 | 0.2 | 0.2 | 0.5 | 1 | 5 |
| | Seed Digestives (l) | 1 | 1 | 1 | 1.0 (7% Slurry 2.8 kg) | 1 | 1 | 1 | 1 | 1 | 1 |
| Charged Manner of Feedstock and Seed Digestives | | Unmixed, layered alternately in strata | | | Mixed (Slurry) | Mixed | | | | | |
| Layer Formation | Feedstock thickness (cm) | 0.5 | 2.5 | 2.5 | | | | | | | |
| | Seed Digestives thickness (cm) | 2.5 | 2.5 | 0.5 | | | | | | | |
| Tank Stirring | | Unstirred | | | Stirred | Unstirred | | Stirred | | | |
| Fermentation Performance | | | | | | | | | | | |
| Methane Yield (l-CH$_4$/kg-feedstock VS) | | 220 | 201 | 179 | 263 | 228 | 58 | 230 | 61 | 43 | 20 |
| Methane Concentration in Fermented Gas (Vol %) | | 47 | 47 | 45 | 50 | 50 | 37 | 50 | 41 | 35 | 16 |
| No. of Days required for Fermentation (d) | | 5 | 10 | 15 | 4 | 7 | 15 | 5 | 12 | 15 | 25 |
| Methane Generation Efficiency in Fermentation Tank (m$^3$-CH$_4$—Fermentation Tank/d-required day) | | 0.71 | 0.98 | 0.97 | 0.40 | 0.29 | 0.06 | 0.75 | 0.17 | 0.14 | 0.08 |
| Feedstock Treatment Efficiency of Fermentation Tank (t-feedstock/m$^3$-fermentation tank/d-required days) | | 0.013 | 0.070 | 0.022 | 0.006 | 0.005 | 0.004 | 0.004 | 0.011 | 0.013 | 0.013 |

According to the present invention, it is possible to ferment solid organic wastes without turning them into slurry and without stirring, so that, as compared with the conventional slurry digestion method, it can widely upgrade the methane productivity per each unit of fermentation tank dimension. Further, it makes large savings possible in the captive consumption of methane which was heretofore used as fuel for the stirrer and heating. In addition to the above, it not only dispenses with the structure for cracking scum and removing sedimentation, but also it facilitates an effective use of fermentive ingredients contained in the digested matter as fertilizer, without wasting into the drain.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A process of anaerobically digesting organic wastes under an anaerobic condition in a digestion tank for recovering methane from said organic wastes by the fermentation effect of said anaerobic bacteria, said process comprising: charging organic wastes having a water content of 50–70% and seed digestives alternatively in a strata formation to said digestion tank said organic wastes formed as a layer between alternating layers of said seed digestives and maintaining the interior of said digestion tank under anaerobic conditions without stirring.

2. A treatment process according to claim 1, wherein said organic wastes are in solid state.

3. A treatment process according to claim 1, wherein said seed digestives are recycled solid digested matters obtained by anaerobically digesting said organic wastes.

4. A treatment process according to claim 2, wherein said seed digestives are recycled solid digested matters obtained by anaerobically digesting said organic wastes.

* * * * *